United States Patent [19]

Altounyan et al.

[11] Patent Number: 4,509,515
[45] Date of Patent: Apr. 9, 1985

[54] INHALATION DEVICE

[75] Inventors: Roger E. C. Altounyan, Wilmslow; Richard M. Auty, Rempstone, both of England

[73] Assignee: Fisons plc, Ipswich, England

[21] Appl. No.: 464,421

[22] Filed: Feb. 7, 1983

[30] Foreign Application Priority Data

Feb. 23, 1982 [GB] United Kingdom ............... 8205240

[51] Int. Cl.³ .......................................... A61M 15/00
[52] U.S. Cl. ........................ 128/200.23; 128/203.15; 604/58; 222/179.5
[58] Field of Search ............... 128/200.23, 203.15; 604/58; 222/179.5, 182, 402.12, 402.13

[56] References Cited

U.S. PATENT DOCUMENTS

| 3,107,670 | 10/1963 | Silson et al. | 128/200.23 |
| 3,209,751 | 10/1965 | Wakeman | 128/200.23 |
| 3,622,053 | 11/1971 | Ryden | 128/200.23 |
| 3,739,950 | 6/1973 | Gorman | 128/200.23 |
| 3,994,421 | 11/1976 | Hansen | 222/402.13 |

OTHER PUBLICATIONS

Fisons Pharmaceutical Division, "Now Intal's Proven Protection Is Delivered More Surely", Fison's Brochure.

Fisons Pharmaceutical Division, "New Intal Spacer", Fisons Brochure.

"The Lung Under Attack", European Society of Pneumology, Second Convention Abstracts, Edinburgh, Sep. 11-16, 1983, p. 76.

Primary Examiner—Henry J. Recla
Attorney, Agent, or Firm—Marshall, O'Toole, Gerstein, Murray & Bicknell

[57] ABSTRACT

There is provided an aerosol inhalation device, suitable for use in association with a pressurized medicament container (10), comprising an elongate member (1) provided at one end with a mouthpiece (5), and adjacent the other end being pivotably connected (3,4) to an aerosol dispenser (2), the aerosol dispenser (2) comprising a body (6) and a spray orifice (9), the elongate member (1) being pivotable to an open inhalation position, in which the spray orifice (9) is directed towards the mouthpiece (5), and to a closed position, in which the elongate member (1) fits around the body (6) of the aerosol dispenser (2), and is of such a length that the mouthpiece (5) is able to fit over the end of the aerosol dispenser (1).

11 Claims, 4 Drawing Figures

INHALATION DEVICE

This invention relates to a device suitable for the administration of an aerosol to the mouth for oral inhalation.

Medicament-containing aerosols, dispensed from pressurised aerosol containers are in widespread use for the relief of various nasal and bronchial disorders such as asthma, hay fever and the like. It is common practice to associate the container, which is filled with a pressurised medicament containing composition and is fitted with a valve, with an applicator, the discharge end of which is shaped to conform to the mouth of the user. In this way, discharge of the medicament-containing aerosol into the mouth is facilitated. Such conventional apparatus may also be provided with means for admitting air into the applicator to ensure scavenging of the medicament-containing aerosol from the applicator, thus helping to provide the patient with the full amount of medicament dispensed from the pressurised container. However, existing pressurised aerosol dispensers suffer from the disadvantages that the patient may well fail to co-ordinate activation of the dispenser and inspiration, or may even breathe out through the mouthpiece. Thus the patient may, often unknowingly, eject the medicament cloud through the air inlet, and thereby fail to take the desired dosage of medicament.

Furthermore, with many existing aerosol inhalation devices a large proportion of the aerosol droplets are deposited on the mucous membranes of the mouth or the trachea instead of being inhaled into the pulmonary system. This may lead to undesirable side effects, for example, infections of the upper airways.

We have now found a new aerosol inhalation device which avoids or mitigates some of the disadvantages of the known aerosol inhalation devices.

According to the invention we provide an aerosol inhalation device, suitable for use in association with a pressurised medicament composition aerosol container, comprising an elongate member provided at one end with a mouthpiece, and adjacent the other end being pivotally connected to an aerosol dispenser, the aerosol dispenser comprising a body and a spray orifice, the elongate member being pivotable to an open inhalation position, in which the spray orifice is directed towards the mouthpiece, and to a closed position, in which the elongate member fits around the body of the aerosol dispenser, and is of such a length that the mouthpiece is able to fit over the end of the aerosol dispenser.

Pressurised medicament composition aerosol containers for use in association with the device according to the invention may be provided with a control valve, preferably a metering valve, and are charged with a medicament-containing, self-propelling liquid composition.

The aerosol dispenser may be of conventional design, comprising an apertured sheath capable of housing a pressurised aerosol container. The sheath is provided internally with an aerosol valve seating connected to the spray orifice, such that actuation of an aerosol container housed in the dispenser causes the pressurised composition to be discharged from the container through the sheath aperture via the spray orifice.

The sheath may have any convenient internal and external cross section, eg oval or rectangular; however we prefer the sheath to have a generally circular internal and external cross-section. The sheath is desirably open at the end remote from the spray orifice to aid actuation and replacement of the aerosol container. We prefer the sheath to be adapted to form a snug fit with the body of the aerosol container.

The side walls of the sheath may be adapted to be co-terminal with, or extend beyond, the non-valve end of an aerosol container housed in the sheath. However, we prefer the sheath to be such that the non-valve end of an aerosol container housed in the sheath protrudes from the sheath by a distance of from about 0.5 to 3.0 cm. This facilitates actuation of the aerosol container.

We prefer the elongate member to be an open trough. We particularly prefer the internal section of the trough to have a partially circular cross-section, preferably from 5° to 200°, more preferably 90° to 195°, most preferably 150° to 190°, and especially of about 180° of arc.

The components of the pivot may be located on any part of the elongate member and aerosol dispenser which permit the inhalation and closed position as defined above to be reached. We prefer the pivot connection to form an elbow joint between the elongate member and the aerosol dispenser.

The elongate member in the inhalation position is preferably at an inclination of from about 80°–120°, preferably about 90° to the longitudinal axis of the dispenser.

We prefer the elongate member and the aerosol dispenser to be lockable in the inhalation position, for example by interaction, such as a snap fit, of a suitably located resilient detente on the elongate member with a corresponding interupted groove on the aerosol dispenser, or vice versa.

The elongate member is preferably provided with a knurl, adjacent the pivot, to help the patient to hold the device when it is in the inhalation position.

When the device is to be used with a conventional cyclindrical pressurised medicament composition aerosol container, of about 2.4 cm diameter, and about 5 cm length, we prefer the length of the elongate member to be from 5 to 10, preferably from 5.5 to 8, and especially 6 to 7 cm, measured from the pivot to the point of attachment of the mouthpiece.

The mouthpiece may be of conventional design. We prefer the mouthpiece to have an unbroken circumference and be generally oval in cross-section.

We particularly prefer the device, in the closed position to form a compact, smooth body, eg where the elongate member and the aerosol dispenser form the two parts of a bisected cylinder. We especially prefer the mouthpiece, elongate member and aerosol dispenser, and any pressurised aerosol container housed therein, to be retained in the closed position by a cap, capable of covering the mouthpiece. The cap may be held in position by the interaction of an appropriately placed tongue on the exterior of the device in the closed position, and a corresponding resiliently flexible groove on the interior of the cap, or vice versa.

A wide variety of medicaments may be used with the device according to the invention, for example:

bronchodilators, eg salbutamol or isoprenaline;

antibiotics, eg tetracycline or penicillin;

topical steroids, eg beclamethasone dipropionate, betamethasone valerate or triamcinolone acetonide;

or particularly an inhibitor of the release and/or action of the pharmacological mediators which result from the in vivo combination of certain types of antibody and specific antigen, eg sodium cromoglycate.

The device according to the invention is advantageous, over similar known devices, because it assists the patient in co-ordinating inhalation with the actuation of the device. Thus a patient failing to correctly co-ordinate inhalation with actuation will be able to see the aerosol cloud around the device, in particular between the mouthpiece and the aerosol dispenser. The device is also advantageous in that it can give improved aerosol dispersion and hence, less deposition of medicament in the mouth, is more easily portable, easier to operate, more convenient to use, or when used in association with a mouthpiece cap, more hygienic, than similar known devices.

The dispersion of an aerosol is defined as the proportion of fine particles in the aerosol cloud smaller than a defined limit, eg 8.5 μm. This gives an indication of the proportion of the aerosol cloud capable of penetration to the deep lung. Dispersion testing is carried out using a single or multi stage impinger following the method described in J Pharm Pharmac 1973, 25, Suppl 32P–36P.

A specific embodiment of the invention will now be described by way of example and with reference to the accompanying drawings, which are not to scale, in which like numerals denote like parts and in which.

Figure 1:
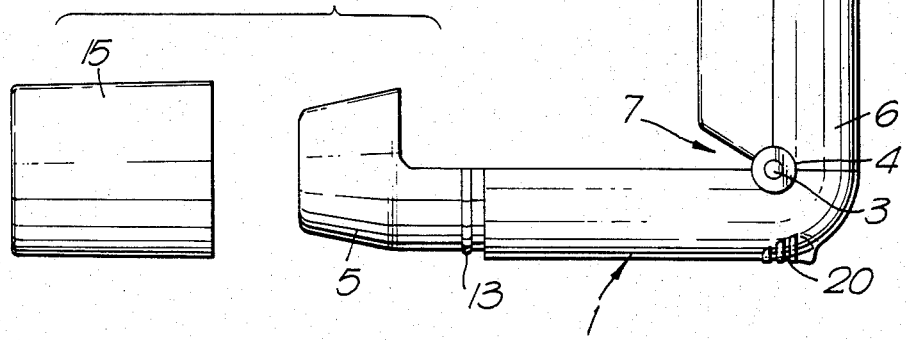
FIG. 1 is a side elevational view of the device, in association with a pressurised aerosol container, in an open position, ready for inhalation.
Figure 2:
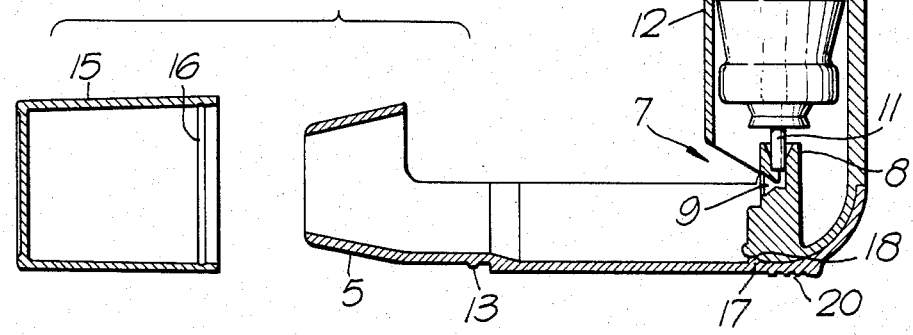
FIG. 2 is a vertical cross-section through the device in FIG. 1.
Figure 3:
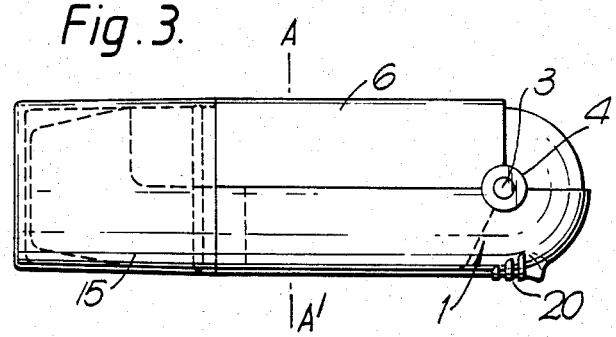
FIG. 3 is a side elevational view of the device in a closed position.
Figure 4:
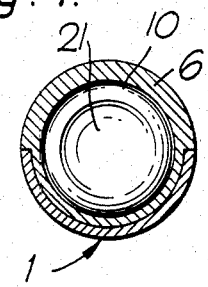
FIG. 4 is a cross-section along the line A, A₁ of FIG. 3.

In the Figures the device comprises a semi-circular trough 1 mounted on an aerosol dispenser 2, by a pivot comprising spigots 3 mounted on the dispenser 2 and interacting with sockets 4 mounted on the trough 1. The trough 1 is provided with a frusto conical mouthpiece 5.

The dispenser 2 comprises a cylindrical sheath 6 provided with an aperture 7. Within the sheath 6, a valve seating 8 is connected to a spray orifice 9. An aerosol container 10, containing a pressurised medicament is provided with a metering valve 11 and is slideably mounted within the sheath 6 so that the valve 11 engages with the seating 8.

The sheath 6 is provided with a half cylindrical recess 12, over which the trough 1 can fit snugly, when the device is in the closed position.

The trough 1 and sheath 6 are each provided with a semi-anular raised lip, respectively 13 and 14, which form a snap fit with a corresponding groove 16 in the cap 15 when the device is in the closed position.

The cap 15 protects the device from contamination by dust and the like.

The device can be locked in the open position by interaction of a detent 17 on the trough 1, with a corresponding recess 18 on the dispenser 2.

A knurled thumb grip 20 helps the patient to hold the device when it is in the inhalation position.

In operation the trough 1 is pivoted to the position shown in FIG. 1. The user places the mouthpiece 5 in his mouth, actuates the aerosol dispenser by pressure between finger and thumb in positions 21 and 20 respectively, and as the aerosol is dispensed into the trough 1, the user inhales the contents of the trough together with a large volume of air. Should the user exhale by mistake the aerosol cloud will be expelled upwards from the trough and will be immediately visible to the user.

The mouthpiece and the sheath may be made from any convenient material, eg metal or preferably a plastics material such as nylon, polypropylene, polyethylene, polystyrene etc. The material of which the mouthpiece and trough is made is preferably not a material which readily acquires and retains a static charge or is preferably treated with an anti-static agent, as excessive static charge will tend to cause the aerosol cloud to precipitate.

We claim:

1. An aerosol inhalation device, suitable for use in association with a pressurized medicament composition aerosol container, comprising in combination an elongate open trough member, a mouthpiece having a continuous tubular wall member and an aerosol dispenser having a body and a spray orifice at the dispenser discharge end, said tubular mouthpiece extending from one end of the elongate open trough member and in axial alignment therewith, and pivot means adjacent the other end of said open trough member for pivotally connecting said other end to the aerosol dispenser body at said discharge end adjacent said spray orifice, the elongate open trough member being pivotally movable between an open inhalation position and a closed position, the spray orifice being directed towards the mouthpiece in the open inhalation position with the open trough member open vertically upward during inhalation use, and in the closed position the elongate open trough member fitting around the body of the aerosol dispenser, and the elongate open trough member being of such a length that the mouthpiece is able to fit over the non-discharge end of the aerosol dispenser said device being suitable for use in association with a cylindrical pressurized medicament composition aerosol container of about 2.4 cm diameter and about 5 cm length, and wherein the length of the elongate open trough member is from 5 to 10 cm, measured from the pivot to the point of attachment of the mouthpiece whereby said open trough portion is of a length sufficient to enable the user to view the open trough portion during inhalation use and detect any medicament escaping upwardly from said open trough portion, thereby indicating the user's failure to coordinate inhalation with actuation of said aerosol dispenser.

2. A device according to claim 1, wherein the aerosol dispenser body comprises a sheath capable of housing a pressurized aerosol container, the sheath being provided with an aperture at the dispenser discharge end adjacent the spray orifice.

3. A device according to claim 2, wherein the sheath is provided internally with an aerosol valve seating connected to the spray orifice, such that actuation of an aerosol container housed in the dispenser causes the pressurized medicament composition to be discharged from the container through the sheath aperture via the spray orifice.

4. A device according to claim 2, wherein the sheath has a circular internal and external cross-section.

5. A device according to claim 2, wherein said sheath is sized such that upon housing an aerosol container the aerosol container will protrude from the sheath by a distance of from about 0.5 to 3.0 cm.

6. A device according to claim 2, wherein the elongate open trough member in the open inhalation position is at an inclination of from about 80°–120° to the longitudinal axis of the dispenser.

7. A device according to claim 1, wherein the open trough member has a partially circular cross-section of from 5° to 200° of arc.

8. A device according to claim 1, wherein the elongate open trough member and the aerosol dispenser are lockable in the inhalation position.

9. A device according to claim 1, wherein the elongate open trough member is provided with a knurl adjacent the pivot, to help a patient to hold the device when it is in the open inhalation position.

10. A device, according to claim 1, wherein the device in the closed position forms a compact, smooth body in which the elongate member and the aerosol dispenser form the two parts of a bisected cylinder.

11. A device, according to claim 1, including a cap, wherein the mouthpiece, elongate open trough member and aerosol dispenser, and any pressurized aerosol container housed therein, are retained in the closed position by said cap, capable of covering the mouthpiece.

* * * * *